(12) United States Patent
Kaethner

(10) Patent No.: US 11,817,213 B2
(45) Date of Patent: Nov. 14, 2023

(54) METHOD FOR COORDINATING A PLURALITY OF REMOTE CONTROL UNITS ON PERFORMANCE OF A PLURALITY OF PRIORITIZED WORKING STEPS

(71) Applicant: Siemens Healthcare GmbH, Erlangen (DE)

(72) Inventor: Christian Kaethner, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 64 days.

(21) Appl. No.: 17/546,291

(22) Filed: Dec. 9, 2021

(65) Prior Publication Data
US 2022/0189628 A1    Jun. 16, 2022

(30) Foreign Application Priority Data
Dec. 15, 2020 (DE) ............ 10 2020 215 938.6

(51) Int. Cl.
*G16H 40/67* (2018.01)
(52) U.S. Cl.
CPC ............... *G16H 40/67* (2018.01)
(58) Field of Classification Search
CPC ........ G16H 40/67; G16H 40/20; G16H 40/60; A61B 6/44; A61B 6/4441; A61B 6/54; A61B 6/548; A61B 34/35; A61B 34/70; H04Q 9/00
USPC .......................................................... 340/4.3
See application file for complete search history.

(56) References Cited

U.S. PATENT DOCUMENTS

| | | | | |
|---|---|---|---|---|
| 8,559,036 B1* | 10/2013 | Khafizova | ............. | G06F 3/1203 358/1.15 |
| 10,769,741 B2* | 9/2020 | Braun | ..................... | H04W 4/90 |
| 2008/0306740 A1* | 12/2008 | Schuck | ................. | G16H 40/67 704/E15.045 |
| 2013/0253951 A1* | 9/2013 | Richter | ................. | G16H 10/60 705/2 |
| 2018/0341393 A1* | 11/2018 | Frenette | ................ | H04W 48/20 |
| 2022/0076851 A1* | 3/2022 | Kamangar | ......... | G06Q 30/0633 |
| 2022/0101218 A1* | 3/2022 | Baumfalk | .......... | G06Q 10/0633 |

FOREIGN PATENT DOCUMENTS

DE    102006017057 A1    10/2007

* cited by examiner

*Primary Examiner* — Omar Casillashernandez
(74) *Attorney, Agent, or Firm* — Harness, Dickey & Pierce, P.L.C.

(57) ABSTRACT

A computer-implemented method is for coordinating a plurality of remote control units on performance of a plurality of prioritized working steps. The method includes receiving a first provisional sequence of the plurality of working steps, at least one remote control unit configured to perform the working step being assigned to at least one working step; receiving an item of information about a status of the at least one assigned remote control unit; prioritizing the plurality of working steps; determining a prioritized sequence of the plurality of working steps based upon the prioritization; providing the prioritized sequence of the plurality of working steps; providing a start signal for the assigned remote control unit for performing the at least one working step of the plurality of working steps. The start signal is here configured to initiate performance of the working step by the assigned remote control unit.

19 Claims, 7 Drawing Sheets

METHOD FOR COORDINATING A PLURALITY OF REMOTE CONTROL UNITS ON PERFORMANCE OF A PLURALITY OF PRIORITIZED WORKING STEPS

PRIORITY STATEMENT

The present application hereby claims priority under 35 U.S.C. § 119 to German patent application number DE 102020215938.6 filed Dec. 15, 2020, the entire contents of which are hereby incorporated herein by reference.

FIELD

Example embodiments of the invention generally relate to a computer-implemented method for coordinating a plurality of remote control units on performance of a plurality of prioritized working steps; and to a coordination system, to a computer program product and to a computer-readable storage medium.

BACKGROUND

On performance of an interventional medical procedure, a clinician or surgeon or physician is typically located close to a treatment subject on which the interventional medical procedure is to be carried out. In other words, the clinician is standing by a treatment table, on which the treatment subject is positioned. In other words, the clinician is located together with the treatment subject in the treatment room. The treatment subject can here, for example, be a human or patient, an animal or an object. The interventional medical procedure here comprises a plurality of working steps which are executed in a sequence. It is known that the clinician is assisted by at least one further clinician, at least one medical assistant and/or at least one imaging system. The imaging system can for example comprise an X-ray system, in particular a C-arm X-ray system or a flat panel X-ray system. The imaging system can alternatively or additionally comprise for example an ultrasound system. The imaging system can alternatively or additionally comprise a magnetic resonance tomography system and/or a computed tomography system and/or a positron emission tomography system and/or a single-photon emission computed tomography system etc.

In recent years, individual interventional medical procedures have been carried out entirely or in part by remote control or remotely. The clinician can here use a remote control unit to control a robotic system with which the interventional medical procedure is carried out on the treatment subject. The remote control unit is typically located in the vicinity of the treatment subject. In recent years, interest has been growing in remote control over greater distances. The remote control unit can here in particular be in another room or another building. In particular, the remote control unit can be spatially distant from the treatment subject. In particular, the remote control unit can be in another city, another country or on another continent than the treatment subject.

Remote control over a greater distance is, however, not yet generally used, since under real-world conditions some problems arise in the case of remote control over large distances. If the clinician is not in situ with the treatment subject, they have, for example, no overview of the overall situation in the treatment room. In particular, they cannot be directly aware of, for example, whether a medical assistant is available, whether treatment material is available, whether the X-ray system is ready etc. It is thus frequently not possible for the clinician to determine a sequence of working steps which is optimized or prioritized for the overall situation or to adapt this sequence to a prevailing situation. In other words, the clinician frequently cannot draw up a prioritized sequence of working steps which is adapted to the overall situation.

SUMMARY

In particular, the inventors have discovered that it would be advantageous if it were possible for the remotely controlled interventional procedure to be performed jointly by a plurality of clinicians. The clinicians can here carry out defined tasks and/or stand by as a substitute in the event of one clinician dropping out. The plurality of clinicians can in particular operate more than one remote control unit. In other words, the clinicians can be in different locations or spatially separate from one another. In other words, spatially separate clinicians operate different remote control units. Communication between clinicians acting spatially separately from one another can often be possible only with difficulty and/or delay. In particular, if a clinician has to stand in for another clinician, rapid notification of the clinician is necessary if they are to be able to respond promptly.

At least one embodiment of the present invention is therefore directed to providing a method which enables prioritization of a sequence of working steps and coordination between a plurality of remote control units or a plurality of clinicians.

Embodiment are directed to a method for coordinating a plurality of remote control units on performance of a plurality of prioritized working steps, by a coordination system for coordinating a plurality of remote control units on performance of a plurality of prioritized working steps; to a computer program product and to a computer-readable storage medium. Advantageous further developments are presented in the claims and in the following description.

Embodiments are achieved according to the invention as described below with regard both to the devices and to the method. Features, advantages or alternative embodiments mentioned in this connection are likewise also transferable to the other subjects and vice versa. In other words, the substantive claims (e.g. directed to a device) can also be further developed with the features which are described or claimed in connection with a method. The corresponding functional features of the method are here formed by corresponding substantive modules.

At least one embodiment of the invention relates to a computer-implemented method for coordinating a plurality of remote control units on performance of a plurality of prioritized working steps. The method comprises a method step of receiving a first provisional sequence of the plurality of working steps with an interface. At least one remote control unit of the plurality of remote control units is here assigned to at least one working step of the plurality of working steps. The assigned remote control unit is here configured to perform the working step. The method moreover comprises a method step of receiving an item of information about a status of at least the assigned remote control unit of the plurality of remote control units with the interface. The method moreover comprises a method step of prioritizing the plurality of working steps at least based upon the first provisional sequence and the information about the status of the assigned remote control unit with a computing unit. The method moreover comprises a method step of determining a prioritized sequence of the plurality of working steps based upon the prioritization with the computing unit. The method moreover comprises a method step of providing the prioritized sequence of the plurality of working steps with the interface. The method moreover comprises a method step of providing a start signal for the assigned remote control unit for performing the at least one working step of the plurality of working steps, wherein the start signal is configured to initiate performance of the working step by the assigned remote control unit.

An embodiment of the invention also relates to a coordination system for coordinating a plurality of remote control units on performance of a plurality of prioritized working steps. The coordination system comprises an interface and a computing unit. The interface is here configured to receive a first provisional sequence of the plurality of working steps. The first provisional sequence here comprises a standard sequence of the plurality of working steps. At least one remote control unit which is configured to perform the working step is here assigned to at least one working step of the plurality of working steps. The interface is moreover configured to receive an item of information about a status at least of the assigned remote control unit of the plurality of remote control units. The computing unit is here configured to prioritize the plurality of working steps at least based upon the first provisional sequence and the information about the status of the assigned remote control unit. The computing unit is moreover configured to determine a prioritized sequence of the plurality of working steps based upon the prioritization. The interface is moreover configured to provide the prioritized sequence of the plurality of working steps. The interface is moreover configured to provide a start signal for the assigned remote control unit for performing the at least one working step of the plurality of working steps. The start signal is here configured to initiate performance of the working step by the assigned remote control unit.

An embodiment of the invention also relates to a computer program product with a computer program and to a computer-readable medium. A largely software-based embodiment has the advantage that coordination systems which are already in service can also straightforwardly be retrofitted to operate in the described manner via a software update. In addition to the computer program, such a computer program product can optionally comprise additional elements such as for example documentation and/or additional components, as well as hardware components, such as for example hardware keys (dongles etc.) for using the software.

In particular, an embodiment of the invention also relates to a computer program product with a computer program which is directly loadable into a memory of a coordination system having program parts for performing all the steps of an embodiment of the described method for coordinating a plurality of remote control units on performance of a plurality of prioritized working steps and the aspects thereof, when the program parts are run by the coordination system.

In particular, an embodiment of the invention relates to a computer-readable storage medium on which program parts readable and runnable by a coordination system are stored in order to perform all the steps of an embodiment of the described method for coordinating a plurality of remote control units on performance of a plurality of prioritized working steps and the aspects thereof, when the program parts are run by the coordination system.

At least one embodiment is directed to a computer-implemented method for coordinating a plurality of remote control units on performance of a plurality of prioritized working steps, the method comprising:

receiving a first provisional sequence of the plurality of working steps via an interface, the first provisional sequence including a standard sequence of the plurality of working steps, wherein at least one remote control unit of the plurality of remote control units, configured to perform the working step, is assigned to at least one working step of the plurality of working steps;

receiving, via the interface, an item of information about a status of at least the at least one remote control, unit of the plurality of remote control units, assigned;

prioritizing, via a computing unit, the plurality of working steps at least based upon the first provisional sequence and the item of information about the status of the at least one remote control unit assigned;

determining, via the computing unit, a prioritized sequence of the plurality of working steps based upon the prioritizing;

providing the prioritized sequence of the plurality of working steps, via the interface; and providing a start signal for the at least one remote control unit assigned, for performing the at least one working step of the plurality of working steps, the start signal being configured to initiate performance of the working step by the at least one remote control unit assigned.

At least one embodiment is directed to a coordination system for coordinating a plurality of remote control units on performance of a plurality of prioritized working steps, comprising:

an interface configured to
 receive a first provisional sequence of the plurality of working steps, the first provisional sequence including a standard sequence of the plurality of working steps, wherein at least one remote control unit of the plurality of remote control units, configured to perform the working step, is assigned to at least one working step of the plurality of working steps, and
 receive an item of information about a status of the at least one remote control unit assigned, of the plurality of remote control units; and a computing unit configured to
 prioritize the plurality of working steps at least based upon the first provisional sequence and the information about the status of the at least one remote control unit assigned, and
 determine a prioritized sequence of the plurality of working steps based upon the prioritization, wherein the interface is further configured to provide the prioritized sequence of the plurality of working steps, and provide a start signal for the at least one remote control unit assigned, for performing the at least one working step of the plurality of working steps, the start signal being configured to initiate performance of the working step by the at least one remote control unit assigned.

At least one embodiment is directed to a non-transitory computer program product storing a computer program, directly loadable into a memory of a coordination system, including program parts for performing the method of claim 1 when the program parts are run by the coordination system.

At least one embodiment is directed to a non-transitory computer-readable storage medium storing program parts, readable and runnable by a coordination system, to perform the method of claim 1 when the program parts are run by the coordination system.

BRIEF DESCRIPTION OF THE DRAWINGS

The above-described properties, features and advantages of this invention will be clearer and more readily comprehensible in connection with the following figures and the description thereof. The figures and description are not intended in any way to limit the invention and the embodiments thereof.

Identical components in different figures are provided with corresponding reference signs. The figures are not in general true to scale.

In the drawings

Figure 1:
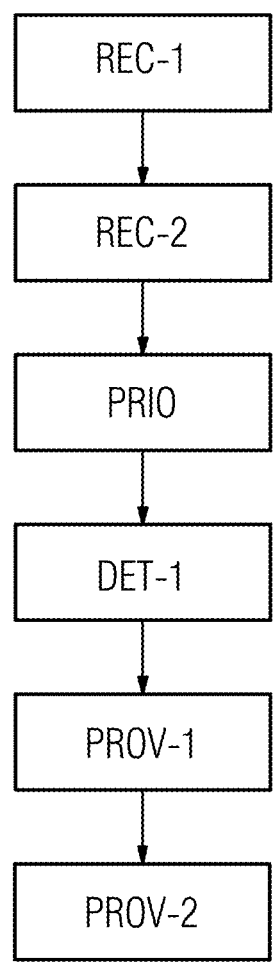
Figure 2:
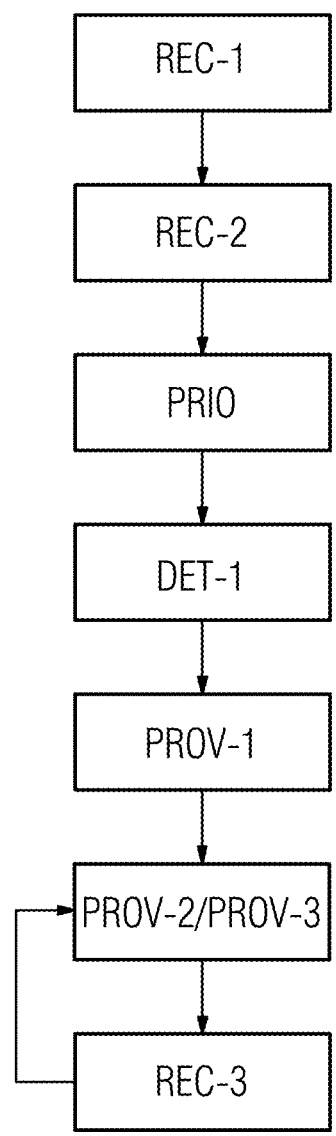
Figure 3:
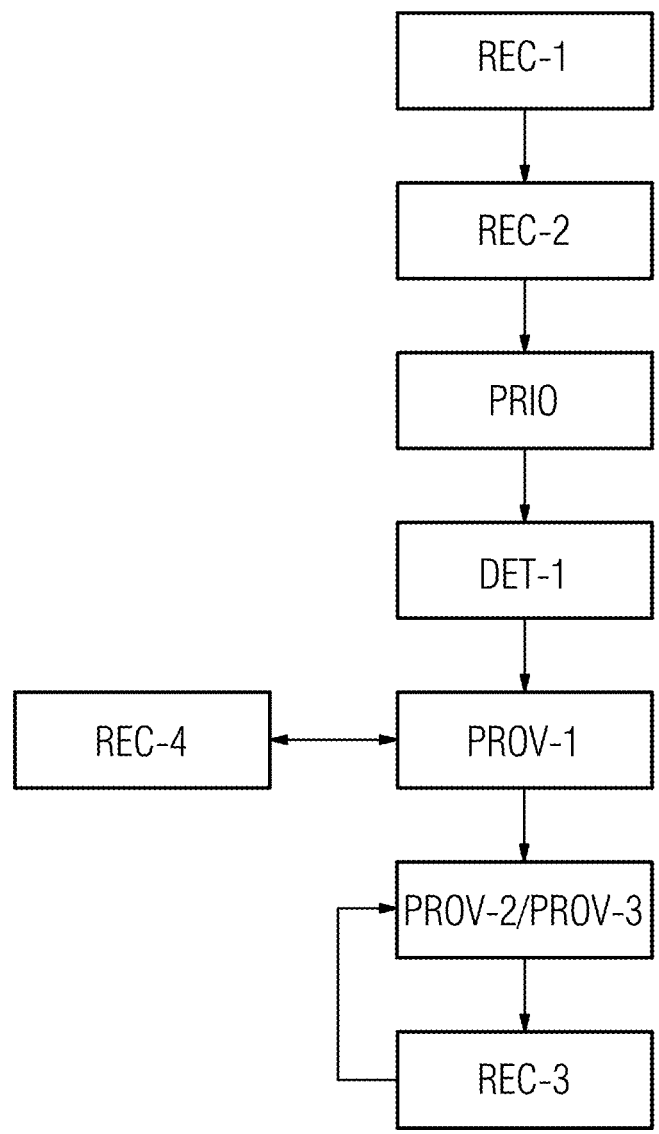
Figure 4:
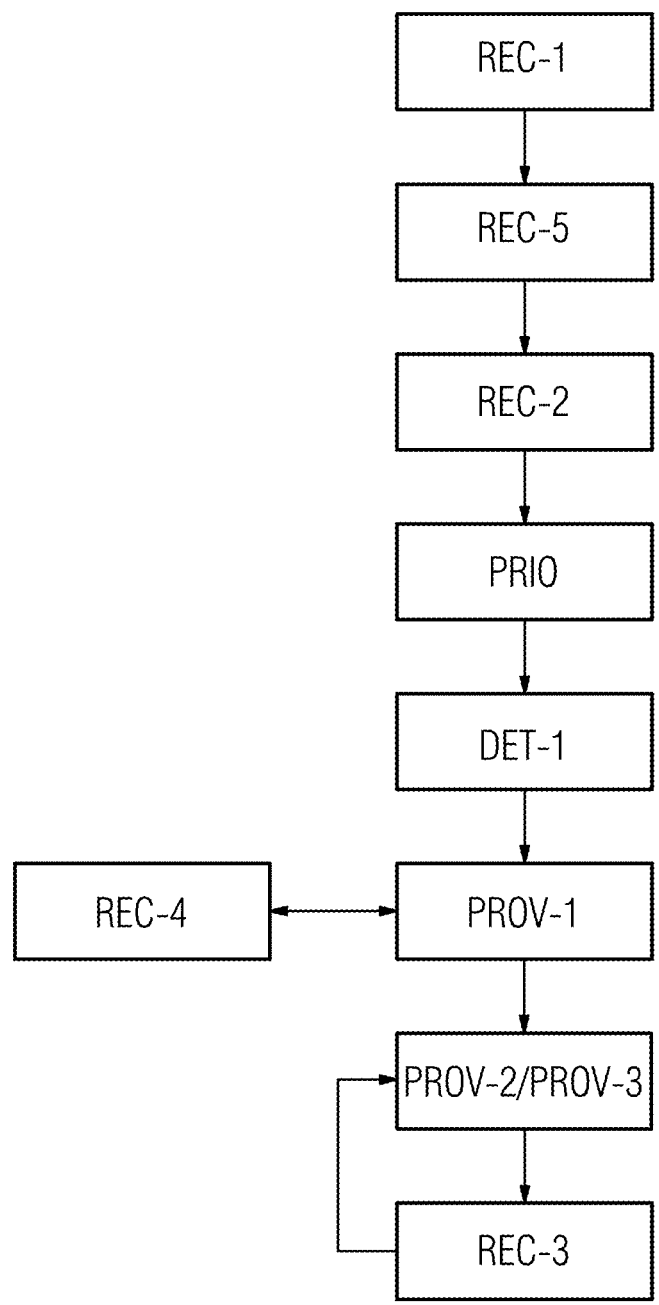
Figure 5:
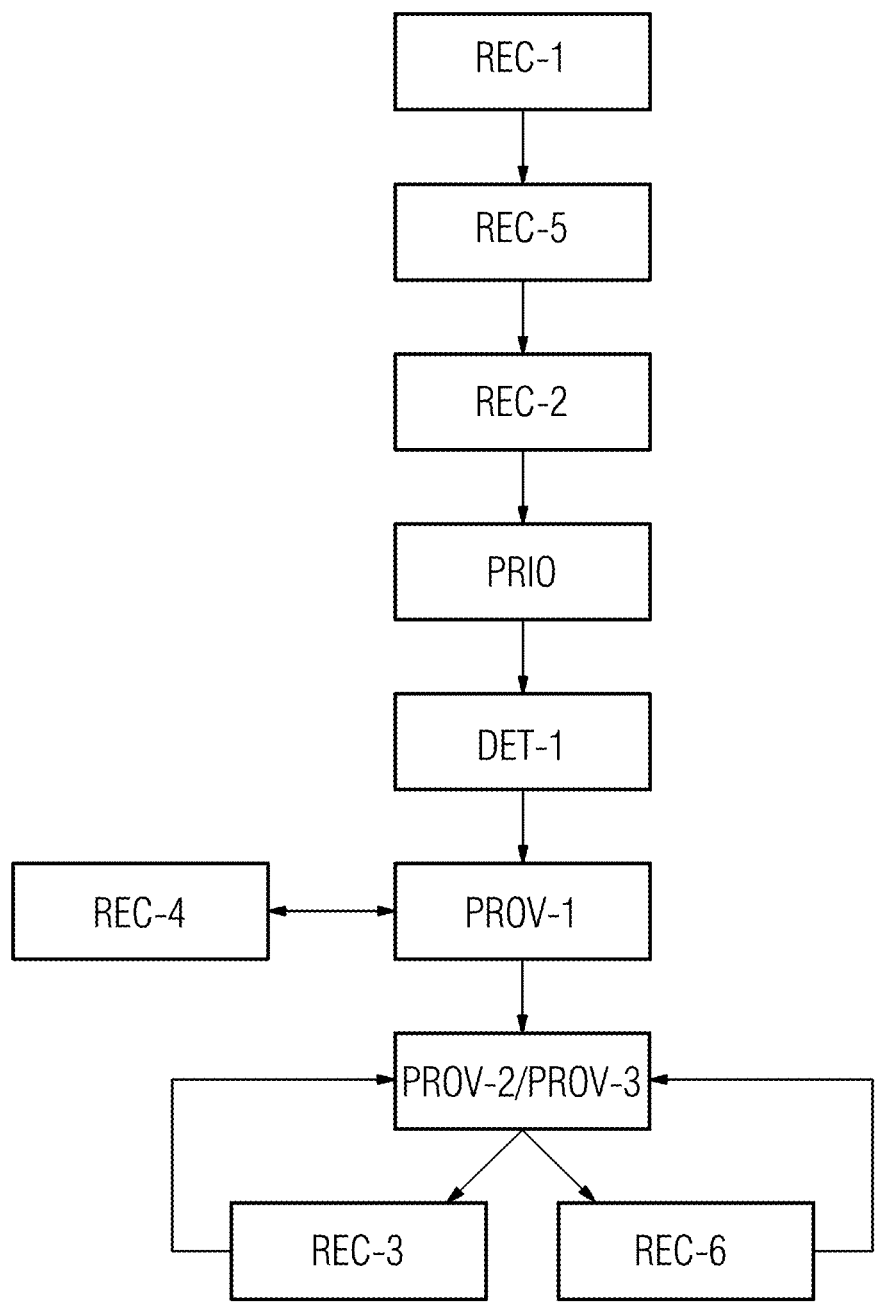
Figure 6:
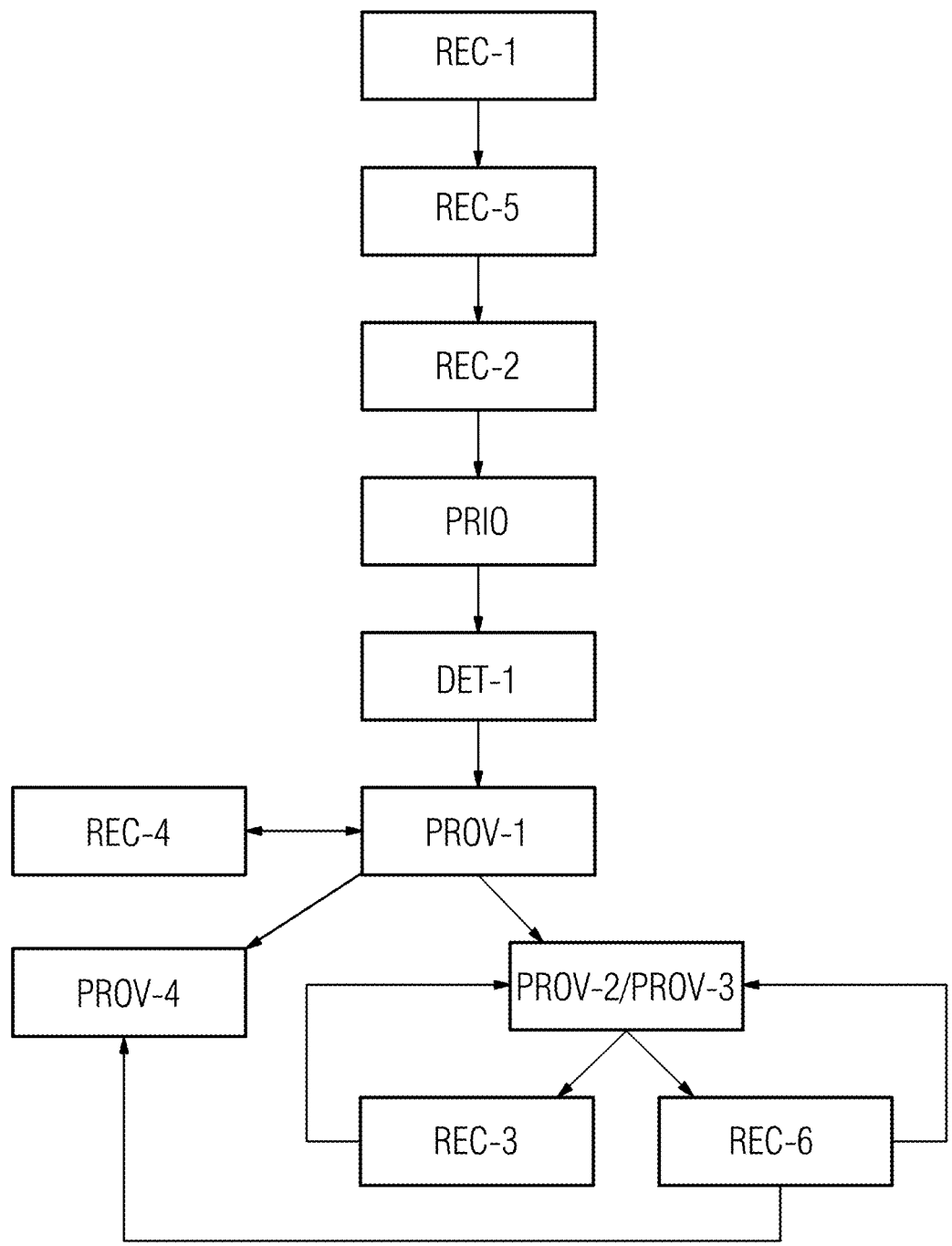
Figure 7:
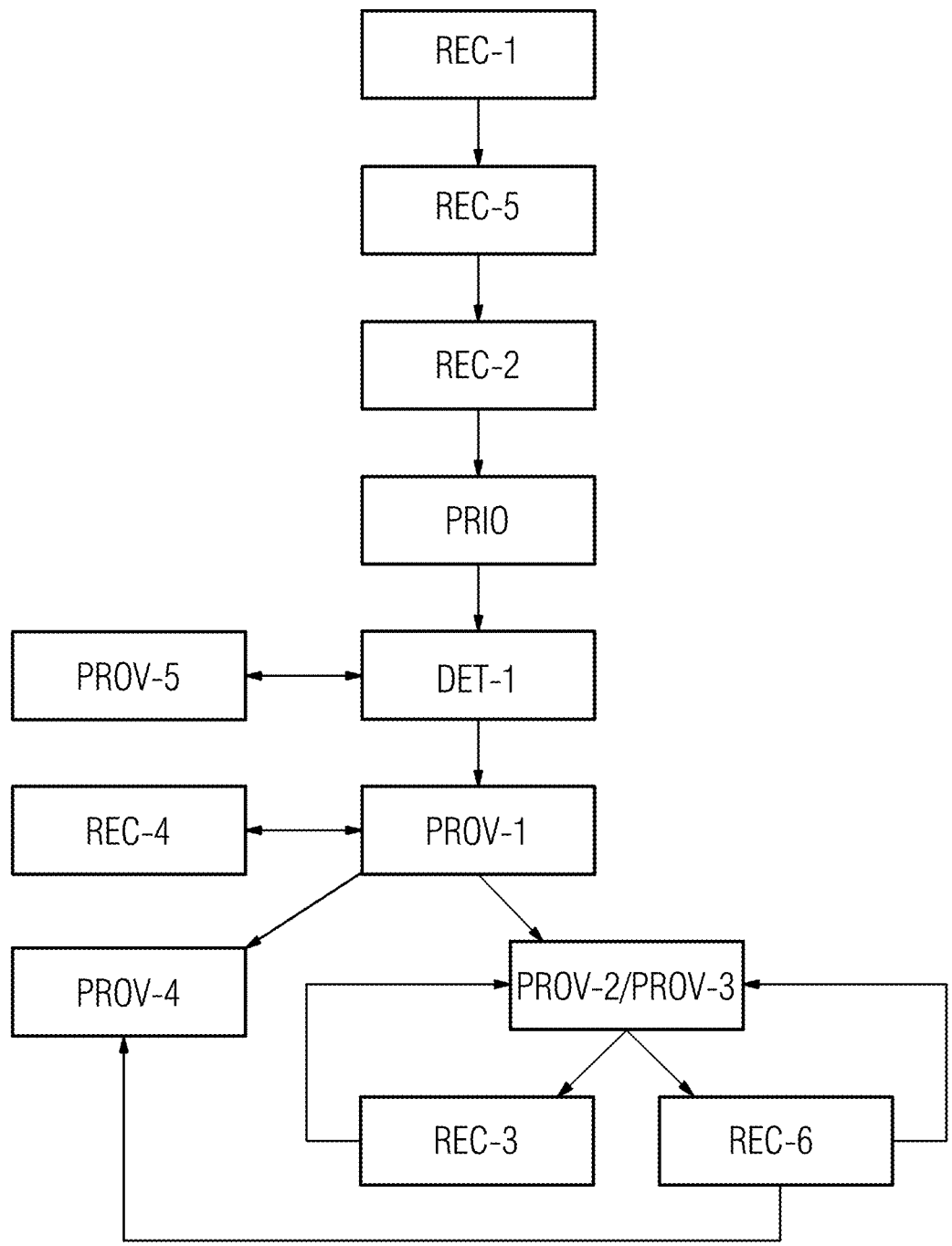
Figure 8:
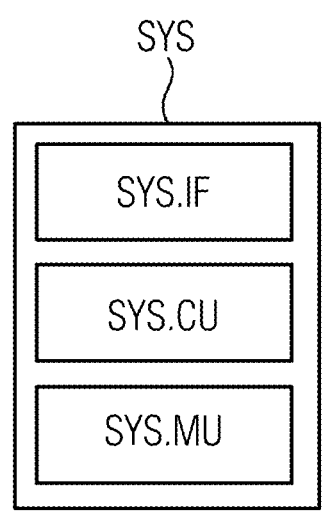

FIG. 1 shows a first example embodiment of a method for coordinating a plurality of remote control units on performance of a plurality of prioritized working steps, FIG. 2 shows a second example embodiment of a method for coordinating a plurality of remote control units on performance of a plurality of prioritized working steps, FIG. 3 shows a third example embodiment of a method for coordinating a plurality of remote control units on performance of a plurality of prioritized working steps, FIG. 4 shows a fourth example embodiment of a method for coordinating a plurality of remote control units on performance of a plurality of prioritized working steps, FIG. 5 shows a fifth example embodiment of a method for coordinating a plurality of remote control units on performance of a plurality of prioritized working steps, FIG. 6 shows a sixth example embodiment of a method for coordinating a plurality of remote control units on performance of a plurality of prioritized working steps, FIG. 7 shows a seventh example embodiment of a method for coordinating a plurality of remote control units on performance of a plurality of prioritized working steps, FIG. 8 shows a coordination system for coordinating a plurality of remote control units on performance of a plurality of prioritized working steps.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a computer-implemented method for coordinating a plurality of remote control units on performance of a plurality of prioritized working steps. The method comprises a method step of receiving a first provisional sequence of the plurality of working steps with an interface. At least one remote control unit of the plurality of remote control units is here assigned to at least one working step of the plurality of working steps. The assigned remote control unit is here configured to perform the working step. The method moreover comprises a method step of receiving an item of information about a status of at least the assigned remote control unit of the plurality of remote control units with the interface. The method moreover comprises a method step of prioritizing the plurality of working steps at least based upon the first provisional sequence and the information about the status of the assigned remote control unit with a computing unit. The method moreover comprises a method step of determining a prioritized sequence of the plurality of working steps based upon the prioritization with the computing unit. The method moreover comprises a method step of providing the prioritized sequence of the plurality of working steps with the interface. The method moreover comprises a method step of providing a start signal for the assigned remote control unit for performing the at least one working step of the plurality of working steps, wherein the start signal is configured to initiate performance of the working step by the assigned remote control unit.

The working steps of the plurality of working steps can in particular be working steps which are carried out in preparation for and/or for follow-up of and/or during an interventional medical procedure. An interventional medical procedure can here be a treatment or examination of a treatment subject, for example of a person or patient or an animal or an object or item. At least one working step of the plurality of working steps can here be performable by a remote control unit of the plurality of remote control units. In other words, at least one working step of the plurality of working steps can be performable via a remote control unit by a clinician operating the remote control unit. The phrases "the clinician performs the working step" and "the remote control unit performs the working step" are here used synonymously. In particular, one or more of the working steps can be performable directly on the treatment subject. In particular, a clinician or a medical assistant can perform one or more working steps of the plurality of working steps directly on the treatment subject without the remote control unit.

A remote control unit of the plurality of remote control units is in particular configured for controlling or remotely controlling a robotic system and/or an imaging system and/or a contrast agent injection system and/or a member of medical personnel. The robotic system can here in particular be a system for carrying out an interventional medical procedure. The imaging system can in particular be configured to carry out an interventional imaging operation. In other words, a medical image or capture of a treatment subject before or after or during the interventional medical procedure can in particular be captured with the imaging system. The imaging system can in particular comprise an X-ray system. The X-ray system can for example comprise a C-arm system and/or a flat panel X-ray system. Alternatively or additionally, the imaging system can comprise a computed tomography device, a magnetic resonance tomography device, an ultrasound device, a positron emission device and/or a single-photon emission computed tomography device. The member of medical personnel can for example be a member of operating room personnel and/or an anesthetist. The member of medical personnel is in particular located in a treatment room close to the treatment subject. The member of medical personnel can be visually and/or acoustically requested via the remote control unit to perform specific working steps on the treatment subject and/or on a medical device, for example the imaging system. In particular, at least one remote control unit of the plurality of remote control units is configured to perform at least one working step for example via the imaging system, via the robotic system, via the contrast agent injection system and/or via the medical personnel. In particular, a clinician can carry out or perform the at least one working step via at least one remote control unit. In particular, the clinician can operate the at least one remote control unit. In particular, the plurality of remote control units can be operated by a plurality of clinicians. In particular, in each case two remote control units of the plurality of remote control units are spatially distant from one another. In particular, this means that two remote control units can for example be arranged in different rooms or buildings. In particular, the two remote control units can be arranged in different cities, in different countries or on different continents. In this case, the clinicians operating the respective remote control unit are also spatially separate.

In the method step of receiving a first provisional sequence of the plurality of working steps, the first provisional sequence of working steps is received with the interface. The first provisional sequence can here in particular comprise a standard sequence of the plurality of working steps. The standard sequence can for example comprise a standardized performance of the interventional medical procedure. The standard sequence can here for example be stored in a database. In particular, at least one standard sequence can be stored for each of a plurality of interventional medical procedures. The standard sequence for the interventional medical procedure to be carried out is in particular then received in the method step of receiving the first provisional sequence. The standard sequence can for example be defined or predetermined by a specification for interventional medical procedures. In particular, the standard sequence can be determined or specified by a Standard Operating Procedure (SOP or guideline) and/or by legal instructions.

At least one remote control unit of the plurality of remote control units can here be assigned to at least one working step of the plurality of working steps. This remote control unit is hereinafter denoted the assigned remote control unit of the plurality of remote control units. In particular, more than one remote control unit of the plurality of remote control units can be assigned to the working step. In embodiments of the invention, at least one remote control unit can be assigned to each of the working steps. Alternatively, at least one working step can be performed in situ on the treatment subject. In other words, at least one working step can be not remotely controllable or remotely performable. In particular, no remote control unit is then assigned to the corresponding working step.

In the method step of receiving an item of information about a status at least of the assigned remote control unit of the plurality of remote control units, the information about the status is received with the interface. The status can here indicate whether and/or at what point in time the assigned remote control unit is available or whether the clinician operating the remote control unit is ready to perform the corresponding working step. This information can in particular be continuously adapted. In particular, the clinician can state if they are not ready to perform the working step. In particular, the information can comprise a downtime or outage time of the at least one assigned remote control unit or a termination of or fault with the connection to the at least one assigned remote control unit. The information about the status of the assigned remote control unit can alternatively or additionally comprise an item of information about the system or the member of medical personnel which/who is controllable with the remote control unit. In particular, the information can comprise a bandwidth for data transmission, an item of information about material stocks, an item of information about availability of the member of medical personnel, an item of information about other remote control units of the plurality of remote control units, an item of information about the systems remotely controllable with the remote control unit, an item of information about the treatment subject, an item of information about a fault, an item of information about an outage and/or an item of information about a complication in the interventional medical procedure.

In the method step of prioritizing the plurality of working steps, the plurality of working steps are prioritized based upon the first provisional sequence and the information about the status of the assigned remote control unit with the computing unit. In other words, prioritization proceeds as a function of the first provisional sequence and the information about the status of the at least one assigned remote control unit. In particular, all the working steps of the plurality of working steps are prioritized. In particular, all the working steps of the first provisional sequence are prioritized. Various working steps can here be equally prioritized. In particular, account can here be taken of whether and/or when the at least one assigned remote control unit is available. Prioritization can here indicate the priority with which an individual working step should be performed. In particular, prioritization can specify an order of the working steps.

In the method step of determining the prioritized sequence of the plurality of working steps, the prioritized sequence is determined with the computing unit based upon the prioritization. The prioritized sequence indicates an optimized sequence or order of the plurality of working steps based upon the first provisional sequence and the information about the status of the at least one assigned remote control unit. Working steps can here in particular be performed simultaneously. In other words, more than one working step can be in the same position in the prioritized sequence. In particular, these working steps can be equally prioritized. The phrase "performance of the prioritized sequence" is hereinafter used analogously to the phrase "performance of the plurality of prioritized working steps".

In the method step of providing the prioritized sequence of the plurality of working steps, the prioritized sequence is provided with the interface. In particular, the prioritized sequence can be provided to at least one clinician of the plurality of clinicians or to another user. In particular, the prioritized sequence can be provided for coordinating the plurality of working steps. In particular, provision can comprise display on a monitor. Alternatively or additionally, provision can comprise saving the prioritized sequence on a data storage medium. The data storage medium can be for example a USB stick, a hard disk, an SD card, a CD, a CD-ROM, a DVD etc. In particular, the prioritized sequence can be saved or stored on a cloud storage system and/or server system. Alternatively or additionally, provision can comprise forwarding the prioritized sequence to another system or unit. In particular, forwarding can proceed over the internet, in particular via LAN and/or WLAN. Alternatively or additionally, the prioritized sequence can be forwarded via mobile radio in particular via LTE and/or 5G.

In the method step of providing the start signal, the start signal for the at least one assigned remote control unit is provided for performing the at least one working step of the plurality of working steps. In particular, if more than one remote control unit is assigned to a working step, the start signal is provided to each of the assigned remote control units or any desired number or subset of the assigned remote control units. The start signal is here configured to initiate performance of the working step by the assigned remote control unit. In particular, the start signal is provided when the at least one working step is to be performed according to the prioritized sequence. In particular, a start signal for the at least one assigned remote control unit can be provided for each working step to which at least one remote control unit is assigned. In particular, the start signals are then provided in the order according to the prioritized sequence. In particular, the start signal can be provided simultaneously for working steps which are to be performed simultaneously or in parallel. In particular, provision of the start signal can comprise display on a monitor of the assigned remote control unit. The start signal can for this purpose take the form of a visual signal, for example as an image and/or text. Alternatively or additionally, the start signal can take the form of an audio signal. In particular, the start signal can be output with a loudspeaker. Alternatively or additionally, the start signal can be a green light or a set of traffic lights changed or switched to green in a room in which the at least one assigned remote control unit is arranged. In particular, the clinician who is operating the at least one assigned remote control unit can be prompted by the start signal to perform the at least one working step with the at least one remote control unit. In particular, the clinician can be prompted to perform the at least one working step manually via the at least one assigned remote control unit. In particular, the start signal can enable the at least one assigned remote control unit to perform the at least one working step. In particular, in some embodiments of the invention the start signal can be provided to each assigned remote control unit.

The inventors have recognized that, based upon the information about the at least one remote control unit and the at least one first provisional sequence in particular of the standard sequence, it is possible to determine a prioritized sequence of the plurality of working steps. The inventors have moreover recognized that a plurality of remote control units can be coordinated by providing the start signal. The inventors have recognized that the prioritized sequence can be determined before the interventional medical procedure. In particular, the prioritized sequence and the assignment of the remote control units can be adapted to a current situation continuously or after fixed time intervals or when triggered by a modification. The modification can, for example, be a change in the status of the assigned remote control unit.

According to one embodiment of the invention, a subset of the plurality of remote control units is assigned to at least one working step. The subset of the plurality of remote control units is here arranged in an order of precedence.

The subset of the plurality of remote control units can in particular comprise a remote control unit. In particular, this remote control unit can be the at least one assigned remote control unit. In particular, the subset can comprise all the remote control units of the plurality of remote control units. In particular, the subset can comprise any desired number of remote control units of the plurality of remote control units. In particular, a second subset of the plurality of remote control units can be assigned to the at least one second working step. In particular, the subsets can be different or identical. In particular, identical or different subsets can be assigned to any desired number of working steps of the plurality of working steps. In particular, each remote control unit of the subset can be configured to perform the at least one working step.

The remote control units of the subset are arranged in an order of precedence. In particular, all the remote control units of the plurality of remote control units can be arranged in an order of precedence. In particular, the order of precedence in different subsets can be identical or different. In particular, the order of precedence can indicate which remote control unit should preferably perform the working step. The order of precedence can moreover indicate which remote control unit should act as the first substitute for the preferred remote control unit. In particular, the order of precedence can indicate the order in which the remote control units should perform the working step by way of substitution in the event of an outage of the preferred remote control unit.

In some embodiments of the invention, the start signal can only be output to the remote control unit which is first in the order of precedence in the assigned subset. In addition, for example in the event of an outage of the preferred or first remote control unit, the start signal can also be output by way of substitution to at least one of the other remote control units of the subset.

The inventors have recognized that it is possible to control by the order of precedence which remote control unit of the subset should preferably perform the at least one working step. Moreover, it is possible to control via the order of precedence which remote control unit should preferably perform the at least one working step by way of substitution in the event of an outage of the preferred remote control unit. The inventors have recognized that the order of precedence can be defined in advance. In particular, no direct communication between clinicians at different remote control units is necessary in the event of an outage of a remote control unit. In particular, with the assistance of the order of precedence, it is possible to decide promptly and without delay which remote control unit should perform the at least one working step by way of substitution.

According to a further embodiment of the invention, the method moreover comprises a method step of detecting an outage of a remote control unit of the subset of the plurality of remote control units. The method moreover comprises a method step of providing the start signal for the remote control unit which, according to the order of precedence, follows the remote control unit which has suffered an outage.

The method step of detecting the outage of the remote control unit involves detecting the outage of that remote control unit which is to perform the at least one working step. In particular, the remote control unit is preferably to perform the at least one working step according to the order of precedence. In particular, the remote control unit is thus a member of the subset of remote control units which are assigned to the working step. In particular, the start signal is provided to the remote control unit. In other words, the start signal is provided to the remote control unit of the subset which is highest or first in the order of precedence. In particular, the outage can be identified or detected by input from the clinician or by a fault with or outage of the connection to the remote control unit. Alternatively or additionally, the outage can be identified by a predefined time interval being exceeded. In particular, the time interval between the start signal and the performance of the working step can be determined. In particular, it is possible to identify if this time interval is becoming too long or exceeds a maximum duration. In particular, this can be identified as outage of the remote control unit.

In the method step of providing the start signal for the remote control unit which, according to the order of precedence, follows the remote control unit which has suffered an outage, the start signal is provided, once an outage of a remote control unit has been detected, to the remote control unit which is next according to the order of precedence. In other words, the start signal is provided to an alternative remote control unit if an outage of the preferred remote control unit has been detected. The alternative remote control unit is defined based upon the order of precedence. Provision of the start signal for the alternative remote control unit initiates performance of the working step by the alternative remote control unit.

The inventors have recognized that, with the assistance of the order of precedence, it is possible to respond rapidly to an outage of a remote control unit and an alternative remote control unit can be prompted to perform the working step by the start signal. In particular, it is possible to determine via the order of precedence which one of the remote control units should preferably perform the working step by way of substitution.

According to a further embodiment of the invention, the method moreover comprises a method step of receiving user input. The user input is here configured to adapt the prioritized sequence and/or order of precedence.

The user input can here be made by the clinician or by one clinician of the plurality of clinicians. Alternatively, the user input can be made by another user, for example a medical assistant. In particular, the user input can be made via a keyboard or a touchpad or a touch-sensitive screen (touch-screen) or a computer mouse. Alternatively or additionally, the user input can be made via speech recognition. In other words, a user's or clinician's voice can be detected, and commands of the user or clinician identified and processed via speech recognition.

The user or clinician can authenticate themselves before and/or during input of the user input. In particular, it is possible in this manner to ensure that the corresponding user or clinician is authorized to adapt the prioritized sequence and/or order of precedence. Authentication can proceed, for example, via automatic user recognition. Automatic user recognition can, for example, proceed via a chip card of the user or clinician, via a fingerprint, via voice recognition, via facial recognition and/or via a password.

In particular, a user or clinician can be prompted to make the user input according to a defined rule. For example, the user or clinician can be prompted to make the user input if they are logged into a specific hospital network and/or if they are available and/or if they are a specialist in an appropriate area of the remotely controlled interventional procedure.

The order of the plurality of working steps can be modified or varied on adaptation of the prioritized sequence. Alternatively or additionally, at least one working step of the plurality of working steps can be removed from the prioritized sequence. Alternatively or additionally, a working step can be added to the prioritized sequence. In particular, adaptation can proceed based upon a list. In particular, a working step which is to be added to the prioritized sequence can be selected from a list. In particular, the prioritized sequence can be provided to the user or clinician for adaptation in the form of a list. A working step of the prioritized sequence is here presented as an element in the list. In particular, the user or clinician can move and/or remove list elements.

The order of precedence can in particular be modified on adaptation of the order of precedence. Alternatively or additionally, a remote control unit can be removed from the subset of remote control units. Alternatively or additionally, a further remote control unit can be added to the subset.

The inventors have recognized that individual adaptation of the prioritized sequence and/or order of precedence is possible by user input. The inventors have recognized that individual aspects can be taken into account on drawing up of the prioritized sequence and/or order of precedence. In particular, clinicians' individual preferences can be taken into account.

According to a further embodiment of the invention, on prioritization, account can be taken of dependencies between the individual working steps.

A dependency between two working steps can, for example, indicate that a specific working step should always be performed before, after or simultaneously with another working step. In particular, dependencies can indicate whether an order of a subset of working steps may be modified. In particular, dependencies can indicate whether at least one other working step may be inserted between two working steps.

The inventors have recognized that account must be taken of dependencies so that the interventional medical procedure is performable with the prioritized sequence.

According to a further embodiment of the invention, a value which characterizes significance is assigned to at least some of the plurality of working steps. A safety-critical value is here assigned high significance. Account is here taken of significance on prioritization.

In particular, significance can indicate which working step or working steps should be treated as prioritized. In other words, significance can indicate which working step or working steps should be closest to the front in the prioritized sequence. Moreover, the start signal can assume a different form as a function of significance. In other words, a safety-critical working step can be characterized as such by the start signal. In particular, the clinician's attention can be drawn to the fact that the working step is safety-critical. Significance can here for example be characterized with a numerical value. For example, a significance of 3 can be high and a significance of 1 low. Alternatively, significance can be characterized for example by the designations "high", "medium" and "low". Alternative, also more finely differentiated, designations for significance are conceivable.

The inventors have recognized that account should be taken of a significance of the working steps on prioritization so that the interventional medical procedure can be carried out safely and appropriately.

According to a further embodiment of the invention, the method moreover comprises a method step of receiving at least one second provisional sequence of the plurality of working steps. The at least one second provisional sequence here comprises an individualized sequence of a user of at least one remote control unit. Prioritization of the plurality of working steps is moreover based on the at least one second provisional sequence.

The plurality of working steps comprised by the second provisional sequence can correspond to the plurality of working steps comprised by the first provisional sequence. Alternatively, the plurality of working steps comprised by the second provisional sequence can differ from the plurality of working steps comprised by the first provisional sequence. In particular, the second provisional sequence can comprise more or fewer working steps than the first provisional sequence.

In particular, the user of the remote control unit can be the clinician. In particular, the clinician or user can provide an individualized sequence as the second provisional sequence. In particular, a second provisional sequence can be received from each clinician of the plurality of clinicians. In particular, the second provisional sequences of the various clinicians can be different.

In particular, account can be taken of an individual circumstance in the second provisional sequence. In particular, this can then be designated an individual sequence. An individual circumstance can for example be a current item of information about the procedure, an item of information about the treatment subject, an item of information about the clinician or clinicians, or technical assistant, an item of information about a technical condition and/or a preference of the clinician. A technical condition can for example be a stability and/or speed of data transmission to the remote control unit.

The second provisional sequence can be drawn up manually by at least one clinician.

Alternatively, the second provisional sequence can be based on a model assumption. The model assumption can model a situation on performance of the plurality of working steps in an individual circumstance. Using the model assumption, the second provisional sequence can be determined based upon the individual circumstances.

Alternatively, the second provisional sequence can be determined with a trained function.

In general, a trained function mimics cognitive functions which people associate with human thinking. In particular, training based on training data can adapt the trained function to new circumstances and recognize and extrapolate patterns.

In general, parameters of a trained function can be adapted via training. In particular, supervised training, semi-supervised training, unsupervised training, reinforcement learning and/or active learning can be used for this purpose. Representation learning, which is alternatively known as feature learning, can furthermore be used. In particular, the parameters of the trained functions can be iteratively adapted by a plurality of training steps.

In particular, a trained function can comprise a neural network, a support vector machine, a random tree or a decision tree and/or a Bayesian network and/or the trained function can be based on k-means clustering, Q-learning, genetic algorithms and/or association rules. In particular, a trained function can comprise a combination of a plurality of uncorrelated decision trees or an ensemble of decision trees (random forest). In particular, the trained function can be determined via XGBoosting (extreme gradient boosting). In particular, a neural network can be a deep neural network, a convolutional neural network or a convolutional deep neural network. A neural network can furthermore be an adversarial network, a deep adversarial network and/or a generative adversarial network. In particular, a neural network can be a recurrent neural network. In particular, a recurrent neural network can be a network with a long short-term memory (LSTM), in particular a gated recurrent unit (GRU). In particular, a trained function can comprise a combination of the described approaches. In particular, the approaches described here for a trained function are denoted the network architecture of the trained function.

The inventors have recognized that at least one individual circumstance can be taken into account by the at least one second provisional sequence. In particular, individual preferences of one or more clinicians can be taken into account via the second provisional sequence on prioritization. The inventors have recognized that in this manner, for prioritization, it is possible to take account not only of the predetermined standard sequence for an interventional medical treatment but also of the information about the at least one assigned remote control unit, as well as individual circumstances. The inventors have recognized that an optimally prioritized sequence can be determined based upon a combination of these three influencing factors. In particular, it is possible to take into account, for example, if data transmission to a clinician is very slow. In particular, any waiting time during data transmission can then be bridged with other working steps. In particular, the interventional medical procedure can inter alia be shortened in this manner.

According to a further optional embodiment of the invention, the method moreover comprises a method step of receiving confirmation of the prioritized sequence.

In particular, the prioritized sequence can be confirmed by confirmation before provision of the start signal. In particular, on confirmation of the prioritized sequence, it is possible to check whether individual working steps in the prioritized sequence are duplicated and/or whether individual working steps in the prioritized sequence are mutually exclusive. In other words, the prioritized sequence can, on confirmation, be checked for inconsistencies. In other words, confirmation indicates that no inconsistencies have been found. In particular, confirmation can comprise a final adaptation of the prioritized sequence.

Confirmation can in particular be provided by a system. The system can be configured to check the prioritized sequence for inconsistencies and optionally correct them.

The system can in particular comprise a trained function which is configured to recognize inconsistencies in a prioritized sequence. Alternatively, confirmation can be provided by a lead clinician. The lead clinician is one clinician of the plurality of clinicians. In particular, the other clinicians of the plurality of clinicians can have a right of veto over a decision of the lead clinician. In particular, the other clinicians can optionally withdraw and/or adapt the confirmation. Alternatively or additionally, confirmation can be provided jointly by the plurality of clinicians. In particular, the clinicians of the plurality of clinicians can come to an agreement about it.

The inventors have recognized that, by receiving confirmation, it is possible to prevent the prioritized sequence from having inconsistencies. In particular, it is possible to prevent the inconsistencies from only coming to light or being identified during the interventional medical procedure.

According to a further embodiment of the invention, prioritization is based on a weighting of the first and at least one second provisional sequence of the plurality of working steps.

In particular, the weighting can be preset. In particular, the weighting indicates how great an influence the individual provisional sequences have on the prioritized sequence. If one of the provisional sequences has a weighting of for example one hundred percent and another provisional sequence has a weighting of zero percent, the prioritized sequence then corresponds to the provisional sequence with a weighting of one hundred percent. In the case of a weighting with a value between one hundred percent and zero percent, a compromise is sought based upon the weighting between the first provisional sequence and the at least one second provisional sequence while taking account of the information about the at least one assigned remote control unit. The provisional sequences are here taken into account in the prioritized sequence according to their weighting. "Provisional sequences" are here taken to mean the first provisional sequence and any second provisional sequences.

The inventors have recognized that weighting the provisional sequences is a simple method for determining the prioritized provisional sequence based upon the first provisional sequence and any second provisional sequences while taking account of the information about the at least one assigned remote control unit.

According to a further embodiment of the invention, prioritization is based on a trained function.

The trained function can in particular be configured as described above. The trained function can in particular have been trained with training input data and training output data. In particular, the trained function can have been trained or adapted during training in such a manner that, on application of the trained function to the training input data, the training output data is generated. The training input data can here be a plurality of first provisional training sequences and associated second provisional training sequences and a plurality of items of training information about assigned remote control units. The training output data can be a plurality of associated prioritized training sequences. The prioritized training sequences can here have been drawn up manually. Alternatively or additionally, the prioritized training sequences can be derived from observation of the clinicians during an interventional medical procedure. In particular, the prioritized sequence can then be determined or produced by applying the trained function to the first provisional sequence and the at least one second provisional sequence and the information about the at least one assigned remote control unit.

In particular, the trained function can be further trained by user input.

The inventors have recognized that, via the trained function, it is possible to provide a continuously trainable method for determining the prioritized sequence. In other words, determination of the prioritized sequence can be continuously improved. In particular, the prioritized sequence can be determined with the trained function without user input or interaction with the clinician or clinicians.

According to a further optional embodiment of the invention, the method moreover comprises a method step of receiving a confirmation of receipt. Receipt of the start signal by the at least one assigned remote control unit is here confirmed by the confirmation of receipt.

In particular, confirmation of receipt can be provided by user input. Alternatively, the at least one assigned remote control unit can automatically acknowledge or confirm receipt of the start signal.

The inventors have recognized that the confirmation of receipt provides a possibility to check whether the start signal has actually been provided. In particular, failure of the confirmation of receipt to materialize allows a technical fault to be rapidly identified and a response provided without a major time delay. In particular, if confirmation of receipt is provided by a user input by the clinician on the at least one assigned remote control unit, it is possible to identify if the clinician does not notice the start signal and/or is not available etc.

According to a further embodiment of the invention, the method moreover comprises a method step of receiving, a confirmation of performance for the initiated working step via the interface, wherein the confirmation of performance indicates that the initiated working step is complete.

The initiated working step is here the working step which was initiated by the start signal. The confirmation of performance indicates that the initiated working step has been completed. Based upon this information, the next working step according to the prioritized sequence can be initiated.

The confirmation of performance can in particular be a manual input by the clinician performing or carrying out the working step. In other words, the clinician can confirm that the initiated working step is complete or finished or has been performed. In particular, the clinician can input the confirmation of performance via a keyboard, a touchpad, a touch-sensitive screen, a computer mouse etc. In particular, after a fixed time interval or waiting interval after initiation of the working step, the clinician can be prompted by the start signal to input a confirmation of performance. In particular, a duration of the waiting interval can be specific to a working step. In particular, failure of the confirmation of performance to materialize within the waiting interval or after prompting can be evaluated as outage of the remote control unit. In particular, the next remote control unit according to the order of precedence can then be provided with the start signal to perform the initiated working step. In particular, the prompt for the clinician to input the confirmation of performance can be canceled. In particular, the waiting interval can start to run again. In particular, the confirmation of performance can be manually input by a medical assistant etc.

Alternatively, confirmation of performance can be provided automatically after a fixed time interval. The time interval can here be specific to the initiated working step. The confirmation of performance can in particular be provided automatically if the performing or carrying out remote control unit performs the initiated working step automatically.

The inventors have recognized that the confirmation of performance enables monitoring of whether the initiated working step has actually been carried out. In particular, the confirmation of performance can optimize performance of the plurality of working steps of the prioritized sequence. Moreover, an outage of a remote control unit can be identified by failure of the confirmation of performance to materialize and appropriate steps can be initiated to continue the interventional medical procedure.

According to a further embodiment of the invention, the method moreover comprises a method step of providing a lockout signal for at least one remote control unit of the plurality of remote control units which is not performing the initiated working step until the confirmation of performance for the initiated working step is received.

In particular, the remote control unit which is performing the initiated working step is the remote control unit which was provided with the start signal.

The lockout signal can in particular be a readout on a monitor. In particular, the lockout signal can prompt a clinician not to undertake any actions on the remote control unit they are operating.

Alternatively or additionally, the lockout signal start can be a red light or a set of traffic lights changed or switched to red in a room in which the corresponding remote control unit is arranged.

Alternatively or additionally, the lockout signal can be configured in such a way that at least one remote control unit which is not performing the initiated working step is locked out for user input or input by the clinician. In particular, the remote control unit can be locked out in such a way that no input is forwarded to the robotic system and/or the imaging system and/or the contrast agent injection system and/or the medical personnel. Alternatively, only emergency input can be forwarded.

In particular, the lockout signal can be output at least to those remote control units in the subset of remote control units assigned to the initiated working step which are not performing the initiated working step. In particular, the lockout signal can be output to all the remote control units of the plurality of remote control units except for the remote control unit which has been provided with the start signal for performing the initiated working step.

The inventors have recognized that the lockout signal prevents more than one clinician from wanting to perform the initiated working step simultaneously on more than one remote control unit. In particular, inconsistencies or uncertainties on performance of the initiated working step can thus be avoided. In particular, performance of the working steps of the plurality of working steps in the prioritized sequence can in this manner be optimized or accelerated. In particular, the interventional medical procedure can in this manner be carried out in accelerated or optimized manner.

According to one optional embodiment of the invention, the method moreover comprises the provision of a ready signal.

In particular, the ready signal or waiting signal can be provided to at least one remote control unit which is to perform the next working step according to the prioritized sequence. In particular, the ready signal can already be provided before provision of the start signal for initiating the corresponding working step. In particular, the ready signal can be provided shortly before the waiting time for an initiated working step has elapsed. In particular, the corresponding clinician can already prepare to perform or carry out the corresponding working step before provision of the start signal.

Alternatively or additionally, the ready signal can be provided to the remote control unit which, according to the order of precedence, follows the remote control unit performing the initiated working step. In particular, it is possible in this manner to signal to the clinician operating this remote control unit that they must stand in in the event of an outage of the performing remote control unit. In particular, the ready signal can be provided if no confirmation of performance is received within the waiting time.

The ready signal can in particular be an amber lamp or a set of traffic lights switched to amber in the room in which the corresponding remote control unit is arranged. Alternatively or additionally, the ready signal can be a readout on a monitor of the remote control unit.

The inventors have recognized that it is possible by the ready signal to signal to a clinician in advance that they shortly have to perform a working step on the remote control unit they are operating. In particular, the clinician can as a result be provided with preparation time in such a way as to interrupt or delay the performance of the prioritized sequence of the plurality of working steps as little as possible.

According to a further embodiment of the invention, receipt of the confirmation of performance and provision of the start signal for the next working step according to the prioritized sequence are initiated until all the working steps of the prioritized sequence have been performed.

In particular, the start signal initiates the first working step according to the prioritized sequence. As soon as the confirmation of performance has been received for the first working step, the next or following working step according to the prioritized sequence is initiated by the start signal. This sequence is carried out until the plurality of working steps according to the prioritized sequence has been performed. If, according to the prioritized sequence, two or more working steps are to be performed simultaneously, they are simultaneously initiated by the start signal. The next working step or steps according to the prioritized sequence are only initiated by the start signal once the confirmations of performance have been received from all the working steps initiated in parallel.

The inventors have recognized that, by providing a start signal as a function of a confirmation of performance of a preceding working step according to the prioritized sequence, it is possible to coordinate a plurality of remote control units in the performance of the prioritized sequence. In particular, the performance of the prioritized sequence can be optimized timewise. In other words, unnecessary intervals between individual working steps can be avoided. In particular, there is no need for the spatially separate clinicians of different remote control units personally to come to an agreement.

According to a further embodiment of the invention, at least one remote control unit of the plurality of remote control units is configured to control an imaging system and/or a robotic system and/or a member of medical personnel and/or a contrast agent injection system etc.

In particular, a clinician can control the imaging system and/or the robotic system and/or the member of medical personnel and/or the contrast agent injection system via the remote control unit. The imaging system and the robotic system can be configured as described above. The medical personnel can, as described above, be trained to perform working steps on the treatment subject. As described above, control here proceeds as a function of the system to be controlled.

The information about the status of the assigned remote control unit can in particular also comprise an item of information about the system or the member of medical personnel which/who is controllable with the remote control unit. In particular, the information can comprise a bandwidth for data transmission, an item of information about material stocks, an item of information about availability of the member of medical personnel, an item of information about other remote control units of the plurality of remote control units, an item of information about the systems remotely controllable with the remote control unit, an item of information about the treatment subject, an item of information about a fault, an item of information about an outage and/or an item of information about a complication in the interventional medical procedure.

The inventors have recognized that a plurality of systems or members of personnel can be controlled with the remote control unit by a spatially remote clinician. In particular, it is possible in this manner for experts in an interventional medical procedure not to have to travel, which means that experts can perform more procedures if they do not have to be in situ each time. Moreover, collaboration between a plurality of experts as clinicians is possible, without all the experts having to be in situ close to the treatment subject. In particular, remote control means that the clinician need not be positioned directly by the treatment subject. In particular in the case of an X-ray monitored interventional medical procedure, it is accordingly possible to ensure that the clinician is not directly exposed to the X-rays during the entire procedure.

According to a further embodiment of the invention, the method moreover comprises a method step of providing an item of requirement information to a further, unassigned remote control unit, wherein the further unassigned remote control unit is required in order to perform the prioritized sequence.

In particular, a user can be informed by the requirement information that none of the remote control units assigned to a working step is configured to perform the working step. In particular, the user can be informed that no remote control unit is assigned to a working step. In particular, the user, for example one of the clinicians, can assign to the corresponding working step a further remote control unit which is configured to perform the working step.

The inventors have recognized that it is possible via the requirement information to ensure that at least the necessary remote control unit is assigned to a working step. In particular, it is possible already in advance of performance of the prioritized sequence of working steps to ensure that all the working steps of the plurality of working steps are performable. In particular, it is possible to ensure that a remote control unit which can perform the corresponding working step is assigned everywhere that one is required.

According to a further optional embodiment of the invention, the method moreover comprises a method step of receiving an item of complication information and a method step of interrupting the performance of the prioritized sequence. The method moreover comprises a optional method step of initiating at least one emergency working step based upon the complication information.

The complication information can in particular describe a complication in the interventional medical procedure. In particular, the complication information can indicate if a complication has occurred. In particular, this can lead to an interruption of the performance of the prioritized sequence. Performance of the prioritized sequence in particular comprises output of the start signal. In particular, performance of the prioritized sequence comprises at least alternating provision of the start signal and receipt of the confirmation of performance until all the working steps of the prioritized sequence have been performed. In particular, performance can be interrupted until the complication has been remedied.

Optionally, at least one emergency working step can be initiated to remedy the complication. The emergency working step can here be inserted into the prioritized sequence at the point at which it has been interrupted. In particular, the emergency working step can be initiated with a start signal in a manner similar to the other working steps of the prioritized sequence. In some embodiments of the invention, a confirmation of performance can indicate when the emergency working step is complete.

In particular, once the complication has been remedied, the prioritized sequence can continue to be performed as described above.

The inventors have recognized that it is possible in this manner to deal with or respond flexibly to complications. In particular, it is possible in this manner flexibly to adapt the prioritized sequence to unplanned circumstances, for example complications.

An embodiment of the invention also relates to a coordination system for coordinating a plurality of remote control units on performance of a plurality of prioritized working steps. The coordination system comprises an interface and a computing unit. The interface is here configured to receive a first provisional sequence of the plurality of working steps. The first provisional sequence here comprises a standard sequence of the plurality of working steps. At least one remote control unit which is configured to perform the working step is here assigned to at least one working step of the plurality of working steps. The interface is moreover configured to receive an item of information about a status at least of the assigned remote control unit of the plurality of remote control units. The computing unit is here configured to prioritize the plurality of working steps at least based upon the first provisional sequence and the information about the status of the assigned remote control unit. The computing unit is moreover configured to determine a prioritized sequence of the plurality of working steps based upon the prioritization. The interface is moreover configured to provide the prioritized sequence of the plurality of working steps. The interface is moreover configured to provide a start signal for the assigned remote control unit for performing the at least one working step of the plurality of working steps. The start signal is here configured to initiate performance of the working step by the assigned remote control unit.

Such a coordination system can in particular be configured to perform an embodiment of the described method for coordinating a plurality of remote control units on performance of a plurality of prioritized working steps and the aspects thereof. The coordination system is configured to perform this method and the aspects thereof by the interface and the computing unit being configured to perform the corresponding method steps.

The interface can in particular comprise one or more than one interface which can perform the various method steps of the method. The computing unit can in particular comprise one or more than one computing unit which can perform the various method steps of the method.

An embodiment of the invention also relates to a computer program product with a computer program and to a computer-readable medium. A largely software-based embodiment has the advantage that coordination systems which are already in service can also straightforwardly be retrofitted to operate in the described manner via a software update. In addition to the computer program, such a computer program product can optionally comprise additional elements such as for example documentation and/or additional components, as well as hardware components, such as for example hardware keys (dongles etc.) for using the software.

In particular, an embodiment of the invention also relates to a computer program product with a computer program which is directly loadable into a memory of a coordination system having program parts for performing all the steps of an embodiment of the described method for coordinating a plurality of remote control units on performance of a plurality of prioritized working steps and the aspects thereof, when the program parts are run by the coordination system.

In particular, an embodiment of the invention relates to a computer-readable storage medium on which program parts readable and runnable by a coordination system are stored in order to perform all the steps of an embodiment of the described method for coordinating a plurality of remote control units on performance of a plurality of prioritized working steps and the aspects thereof, when the program parts are run by the coordination system.

FIG. 1 shows a first example embodiment of a method for coordinating a plurality of remote control units on performance of a plurality of prioritized working steps.

A remote control unit of the plurality of remote control units is configured to control, for example, an imaging system, a robotic system, a contrast agent injection system and/or a member of medical personnel. Control can in this case comprise electronic control and/or control via a visual and/or acoustic readout. In particular, a remote control unit can perform a working step. One of the above-stated systems or medical personnel can be controlled to perform the working step. At least two remote control units of the plurality of remote control units can be positioned or arranged spatially separately from one another. In other words, the remote control units can be arranged or positioned in different rooms or in different buildings or in different cities or in different countries or on different continents. A remote control unit can be operated by a clinician. In particular, the clinician can thus perform the working step with the remote control unit. In particular, the plurality of remote control units can be operated by a plurality of clinicians.

The plurality of working steps can be performed by the plurality of remote control units. The plurality of working steps can for example be at least one part of an interventional medical procedure. The interventional medical procedure can be carried out on a treatment subject, for example a human or patient, an animal or an object. The working steps of the plurality of working steps can here be prioritized according to the method. In other words, the working steps can be put into an (optimized) order or sequence. The plurality of prioritized working steps is thus arranged in a prioritized or optimized sequence.

In a method step of receiving REC-1 a first provisional sequence of the plurality of working steps, the first provisional sequence is received with an interface SYS.IF. The first provisional sequence describes a standard sequence of the plurality of working steps. The standard sequence can be predetermined for example by a medical guideline (standard operating procedure, SOP) or by legal instructions. In particular, the first provisional sequence can be stored in a database. The first provisional sequence can be specific to an interventional medical procedure. In particular, different first provisional sequences can be stored for different interventional medical procedures.

At least one remote control unit is here assigned to at least one working step of the plurality of first working steps. In particular, a subset of the plurality of remote control units can be assigned to the working step. The subset can here in particular comprise one or all of the remote control units. The at least one assigned remote control unit is in particular configured to perform the working step. In other words, the clinician who is operating the at least one assigned remote control unit is trained to perform the working step. In particular, at least one remote control unit can be assigned to more than one working step of the plurality of working steps. In particular, a remote control unit can be assigned to each of the working steps. Advantageously, a remote control unit is assigned to each working step which is performable by remote control.

In particular, the subset of remote control units can be arranged in an order of precedence. In particular, all the remote control units of the plurality of remote control units can be arranged in an order of precedence. In particular, the order of precedence in the subset can depend on the order of precedence of all the remote control units. Alternatively, the order of precedence can differ for each working step. In particular, the order of precedence can indicate a prioritization of the remote control units on performance of the working step to which they are assigned. In other words, the order of precedence can indicate which remote control unit of the assigned subset of remote control units should ideally perform the corresponding working step. In particular, it is possible to control with the order of precedence which remote control unit should take over performance of the working step by way of substitution. In particular, the remote control units take over performance of the working step according to the order of precedence.

In a method step of receiving REC-2 an item of information about a status of at least the assigned remote control unit of the plurality of remote control units, an item of information about the status of at least the assigned remote control unit is received with the interface SYS.IF. The status can here in particular be an availability of the assigned remote control unit and/or an outage of the assigned remote control unit. In particular, the information about the status can also comprise an item of information about a status of the systems or medical personnel controlled by the assigned remote control unit. For example, the information can comprise an item of information about a bandwidth for data transmission and/or an item of information about material stocks and/or an item of information about the medical personnel and/or an item of information about the plurality of (assigned) remote control units and/or an item of information about the treatment subject and/or an item of information about a fault and/or an item of information about a complication etc. In particular, the information about the status of the at least one assigned remote control unit may also comprise an item of information about whether the clinician operating the remote control unit is ready to perform the working step.

In a method step of prioritizing PRIO the plurality of working steps, the plurality of working steps are prioritized based upon the first provisional sequence and the information about the status of the assigned remote control units with a computing unit SYS.CU. In other words, on prioritization PRIO of the plurality of working steps, account is taken of at least the first provisional sequence and the information about the status of the at least one assigned remote control unit. If more than one remote control unit is assigned to the plurality of working steps, account is taken of the information about the status of each of the assigned remote control units. In particular, account is taken of a significance or importance of the working steps on prioritization PRIO. In particular, an elevated significance can be assigned to safety-critical working steps. In particular, on prioritization PRIO, account can be taken of dependencies between individual working steps. A dependency can in particular describe that one working step has to be performed before another working step. Alternatively or additionally, a dependency can indicate whether a further working step may be performed between two working steps. Alternatively or additionally, a dependency can indicate whether two or more working steps should be performed in parallel. In particular, two or more working steps can be identically prioritized for this purpose.

In a method step of determining DET-1 a prioritized sequence of the plurality of working steps, the prioritized sequence is determined with the computing unit SYS.CU based upon the prioritization PRIO. The prioritized sequence indicates an order of the plurality of working steps which is determined based upon the prioritization PRIO. In particular, the prioritized sequence thus takes account of at least the first provisional sequence and the information about the status of the at least one assigned remote control unit. The prioritized sequence can also be denoted prioritized working steps.

In a method step of providing PROV-1 the prioritized sequence of the plurality of working steps, the prioritized sequence is provided with the interface SYS.IF. In particular, the prioritized sequence can be provided to a user, for example at least one clinician of the plurality of clinicians. In particular, the prioritized sequence can be provided on a monitor. In other words, the prioritized sequence can be displayed. Alternatively or additionally, the prioritized sequence can be stored on a data storage medium. The data storage medium can in particular be a USB stick, an SD card, a CD, a CD-ROM, a DVD or a fixed disk (for example hard disk (HD) or solid state disk (SSD)). Alternatively or additionally, the prioritized sequence can be provided to a computer system. For example, the prioritized sequence can be provided to a computer system comprised by an imaging system.

In a method step of providing PROV-2 a start signal for performing the at least one working step of the plurality of working steps, the start signal is provided to the assigned remote control unit. The start signal is configured to initiate performance of the working step by the remote control unit. If more than one remote control unit is assigned to the working step, the start signal can in particular be provided to a selected remote control unit of the subset of remote control units. In particular, the one selected remote control unit can be selected with the assistance of the order of precedence. In particular, the start signal can be output to the remote control unit with the highest rank in the order of precedence. Alternatively, the start signal can be provided to each remote control unit of the subset of remote control units.

FIG. 2 shows a second example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1.

In a method step of detecting REC-3 an outage of a remote control unit of the subset of the plurality of remote control units, it is detected if a remote control unit assigned to a working step suffers an outage. The subset of the plurality of remote control units corresponds to the set of remote control units which is assigned to the working step to be performed. The working step to be performed is the working step which is to be performed next according to the prioritized sequence. An outage can in particular be detected by an absence of feedback from the remote control unit or the clinician operating the remote control unit and/or by an error message and/or by an input by the clinician etc. In particular, this method step detects outage of the remote control unit which, according to the order of precedence, is to perform the working step to be performed. In other words, it is detected if the remote control unit which is responsible according to the order of precedence cannot perform the working step to be performed.

In a method step of providing PROV-3 the start signal for the remote control unit which, according to the order of precedence, follows the remote control unit which has suffered an outage, the start signal is provided to the remote control unit which is to perform the corresponding working step by way of substitution. The provision PROV-3 of the start signal for the substitute remote control unit may proceed in a manner similar to the method step of providing PROV-2 the start signal for the assigned remote control unit.

In other words, it is possible, by performing the two method steps, to activate the remote control units assigned to a working step in accordance with the order of precedence, as soon as one of the remote control units suffers an outage or is unavailable.

FIG. 3 shows a third example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1. The method steps of detecting REC-3 an outage of a remote control unit and of providing PROV-3 the start signal for the remote control unit which, according to the order of precedence, follows the remote control unit which has suffered an outage are configured according to the description relating to FIG. 2.

In a method step of receiving REC-4 a user input, the user input which is configured to adapt the prioritized sequence and/or the order of precedence is received. The user can here in particular be the clinician or clinicians. Alternatively, the user can be a medical assistant or a physician etc. In particular, the user can, via the user input, adapt the prioritized sequence to their preferences. In particular, the user can check whether the prioritized sequence complies with the legal instructions or the guideline and, if necessary, adapt them. The order of precedence can be adapted for example as a function of the clinicians operating the remote control units. In particular, the order of precedence can be adapted in the event of a longer term outage of a remote control unit.

The user input can in particular be made via a keyboard, a touchpad, an input with a computer mouse or a touch-sensitive screen.

FIG. 4 shows a fourth example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1. The method steps of detecting REC-3 an outage of a remote control unit and of providing PROV-3 the start signal for the remote control unit which, according to the order of precedence, follows the remote control unit which has suffered an outage are configured according to the description relating to FIG. 2. The method step of receiving REC-4 a user input can be configured according to the description relating to FIG. 3.

In a method step of receiving REC-5 at least one second provisional sequence of the plurality of working steps, at least one second provisional sequence of working steps is received. The second provisional sequence is here an individualized sequence of a user of a remote control unit. The user can here in particular be the clinician. The plurality of working steps comprised by the second provisional sequence can differ from the plurality of working steps comprised by the first provisional sequence. The second provisional sequence can in particular correspond to the preferences of the clinician or user. On drawing up the second provisional sequence, the user can in particular adapt the standard sequence according to their preferences. In particular, a second provisional sequence can be received from more than one user or clinician. In particular, a second provisional sequence can be received from each clinician of the plurality of clinicians. In particular, the second provisional sequences from different clinicians are different.

On prioritization PRIO, the plurality of working steps is prioritized based upon the first provisional sequence, the second provisional sequence and the information at least about the status of the at least one assigned remote control unit. In other words, account is taken of the first provisional sequence, the second provisional sequence and the information at least about the status of the at least one assigned remote control unit. In particular, account is thus taken of individual preferences of the clinician or clinicians on prioritization PRIO and thus also on determination DET-1 of the prioritized sequence.

Prioritization PRIO can here be based on a weighting of the first and the at least one second provisional sequence. The influence of the provisional sequences on prioritization PRIO can be regulated via the weighting.

Alternatively or additionally, prioritization PRIO can be based on a trained function. In particular, the trained function can receive the provisional sequences and the information about at least the status of the at least one assigned remote control unit as input data. In particular, the trained function can prioritize PRIO the plurality of working steps based upon the input data. In some embodiments of the invention, the trained function can also determine the prioritized sequence.

FIG. 5 shows a fifth example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1. The method steps of detecting REC-3 an outage of a remote control unit and of providing PROV-3 the start signal for the remote control unit which, according to the order of precedence, follows the remote control unit which has suffered an outage are configured according to the description relating to FIG. 2. The method step of receiving REC-4 a user input can be configured according to the description relating to FIG. 3. The method step of receiving REC-5 the at least one second provisional sequence can be configured according to the description relating to FIG. 4.

In a method step of receiving REC-6 a confirmation of performance, the confirmation of performance for the initiated working step is received via the interface SYS.INF. The confirmation of performance here indicates that the initiated working step is complete. The confirmation of performance can here be provided manually by the clinician who is to perform the working step with the assigned remote control unit. In particular, the clinician can be prompted after a waiting interval to provide or send or confirm the confirmation of performance. The waiting interval can have a specific duration for each working step. The waiting interval can start to run with the provision of the start signal for the working step. The clinician can optionally extend or restart the waiting interval. Alternatively, the confirmation of performance can be provided automatically once the waiting interval has elapsed. However, this only makes sense if the working step proceeds fully automatically. In particular, failure of the confirmation of performance to materialize can be detected as an outage of the corresponding remote control unit.

Receipt REC-6 of the confirmation of performance initiates the provision PROV-2 of the start signal for the next working step according to the prioritized sequence. This is in particular depicted in the figure by the arrow between the method step of receiving REC-6 the confirmation of performance and provision PROV-2 of the start signal.

After provision PROV-2 of the start signal, it is thus possible either to detect an outage of the remote control unit or to await receipt REC-6 of the confirmation of performance. The two loops are performed until all the working steps of the prioritized sequence have been performed.

FIG. 6 shows a sixth example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1. The method steps of detecting REC-3 an outage of a remote control unit and of providing PROV-3 the start signal for the remote control unit which, according to the order of precedence, follows the remote control unit which has suffered an outage are configured according to the description relating to FIG. 2. The method step of receiving REC-4 a user input can be configured according to the description relating to FIG. 3.

The method step of receiving REC-5 the at least one second provisional sequence can be configured according to the description relating to FIG. 4. The method step of receiving REC-6 a confirmation of performance can be configured according to the description relating to FIG. 5.

In a method step of providing PROV-4 a lockout signal, the lockout signal is provided to the plurality of remote control units which are not performing the initiated working step. The lockout signal is provided until the confirmation of performance has been received. In particular, the lockout signal is provided to the remote control units of the subset of the remote control units assigned to the working step to be performed and to which the start signal has not been provided. The lockout signal can in particular be a visual and/or acoustic signal. In particular, the lockout signal can be a readout on a screen or monitor. Alternatively or additionally, the lockout signal can comprise blocking the remote control unit. Alternatively or additionally, the lockout signal can be a red lamp or a set of traffic lights switched to red. The lockout signal prevents a plurality of remote control units from simultaneously performing the same working step. The lockout signal can be canceled for a remote control unit before receipt REC-6 of the confirmation of performance if, according to the order of precedence, the remote control unit is to take over performance of the working step from a remote control unit which has suffered an outage. In particular, provision PROV-3 of the start signal can override the lockout signal.

FIG. 7 shows a seventh example embodiment of a method for coordinating a plurality of remote control units on performance of a plurality of prioritized working steps.

The method steps of receiving REC-1 a first provisional sequence of the plurality of working steps, of receiving REC-2 an item of information about a status of at least the assigned remote control units, of prioritizing PRIO the plurality of working steps, of determining DET-1 a prioritized sequence, of providing PROV-1 the prioritized sequence and of providing PROV-2 a start signal are configured according to the description relating to FIG. 1. The method steps of detecting REC-3 an outage of a remote control unit and of providing PROV-3 the start signal for the remote control unit which, according to the order of precedence, follows the remote control unit which has suffered an outage are configured according to the description relating to FIG. 2. The method step of receiving REC-4 a user input can be configured according to the description relating to FIG. 3. The method step of receiving REC-5 the at least one second provisional sequence can be configured according to the description relating to FIG. 4. The method step of receiving REC-6 a confirmation of performance can be configured according to the description relating to FIG. 5. The method step of providing PROV-4 a lockout signal is configured according to the description relating to FIG. 6.

In a method step of providing PROV-5 an item of requirement information, the requirement is provided to a further, unassigned remote control unit. The further remote control unit is here required to perform the prioritized sequence. In particular, it is possible to identify on determination DET-1 of the prioritized sequence if one of the working steps of the plurality of prioritized working steps cannot be performed because no remote control unit has been assigned or because the assigned remote control unit is not configured to perform the working step or because the assigned remote control unit has suffered an outage. The requirement information indicates the working step to which a suitable further remote control unit must be assigned so that the prioritized sequence can be performed. The further remote control unit can be part of the plurality of remote control units. Alternatively, the further remote control unit can still be unknown. In particular, one of the clinicians or a medical assistant can optionally add the further remote control unit and assign it to the corresponding working step.

FIG. 8 shows a coordination system SYS for coordinating a plurality of remote control units on performance of a plurality of prioritized working steps.

The system SYS shown for coordinating a plurality of remote control units on performance of a plurality of prioritized working steps is configured to perform a method according to an embodiment of the invention for coordinating a plurality of remote control units on performance of a plurality of prioritized working steps. The system SYS comprises an interface SYS.IF, a computing unit SYS.CU and a memory unit SYS.CU.

The system SYS can in particular be a computer, a microcontroller or an integrated circuit (IC). Alternatively, the system SYS can be a real or virtual computer network (a technical name for a real computer network is "cluster" and a technical name for a virtual computer network is "cloud"). The system SYS can be configured as a virtual system which is run on a computer or a real computer network or a virtual computer network (a technical name is "virtualization").

The interface SYS.IF can be a hardware or software interface (e.g. a PCI bus, USB or FireWire). The computing unit SYS.CU can comprise hardware and/or software components, for example a microprocessor or a field programmable gate array (FPGA). The memory unit SYS.CU can be configured as a volatile working memory (random access memory, RAM) or as a non-volatile mass storage device (hard disk, USB stick, SD card, solid state disk (SSD)).

The interface SYS.IF can in particular comprise a plurality of subinterfaces which carry out different method steps of the respective method according to an embodiment of the invention. In other words, the interface SYS.IF can take the form of a plurality of interfaces SYS.IF. The computing unit SYS.CU can in particular comprise a plurality of subcomputing units which carry out different method steps of the respective method according to an embodiment of the invention. In other words, the computing unit SYS.CU can take the form of a plurality of computing units SYS.CU.

Where it has not yet been explicitly done but is reasonable and in line with the purposes of the invention, individual example embodiments, individual sub-aspects or features thereof can be combined with one another or interchanged without going beyond the scope of the present invention. Advantages of the invention described in relation to one example embodiment also apply, where transferable, to other example embodiments without being explicitly stated to do so.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for coordinating a plurality of remote control units on performance of a plurality of working steps, the method comprising:
   receiving a first provisional sequence of the plurality of working steps via an interface, the first provisional sequence including a sequence of the plurality of working steps, wherein at least one remote control unit of the plurality of remote control units, configured to perform the plurality of working steps, is assigned to at least one working step of the plurality of working steps;
   receiving, via the interface, an item of information about a status of at least the assigned at least one remote control unit;
   prioritizing, via a computing unit, the plurality of working steps at least based upon the first provisional sequence and the item of information;
   determining, via the computing unit, a prioritized sequence of the plurality of working steps based upon the prioritizing;
   providing the prioritized sequence of the plurality of working steps, via the interface;
   providing a start signal for the assigned at least one remote control unit, the start signal configured to initiate performance of the at least one working step by the assigned at least one remote control unit;
   receiving a confirmation of performance for the initiated at least one working step, the confirmation of performance indicating that the initiated at least one working step is complete; and
   providing a lockout signal for at least one remote control unit of the plurality of remote control units that is not performing the initiated at least one working step until all of the plurality of working steps of the prioritized sequence have been performed.

2. The method of claim 1, wherein a subset of the plurality of remote control units is assigned to at least one working step, and wherein the subset of the plurality of remote control units is arranged in an order of precedence.

3. The method of claim 2, further comprising:
   detecting an outage of a remote control unit of the subset of the plurality of remote control units; and
   providing the start signal for the remote control unit which, according to the order of precedence, follows the remote control unit that has suffered an outage.

4. The method of claim 2, further comprising:
   receiving a user input configured to adapt at least one of the prioritized sequence or the order of precedence.

5. The method of claim 1, wherein the prioritizing includes taking account of dependencies between individual working steps of the plurality of working steps.

6. The method of claim 1, further comprising:
   assigning a value characterizing significance to at least some of the plurality of working steps; and
   assigning a high significance to a safety-critical working step,
   wherein the prioritizing includes taking account of the significance of the plurality of working steps.

7. The method of claim 1, further comprising:
   receiving at least one second provisional sequence of the plurality of working steps,
   wherein the at least one second provisional sequence includes an individualized sequence of a user of at least one remote control unit, and
   wherein the prioritizing include prioritizing the plurality of working steps based on the at least one second provisional sequence.

8. The method of claim 7, wherein the prioritizing includes prioritizing the plurality of working steps based on a weighting of the first provisional sequence and the at least one second provisional sequence of the plurality of working steps.

9. The method of claim 1, wherein the prioritizing includes prioritizing the plurality of working steps based on a trained function.

10. The method of claim 1, further comprising
    initiating receipt of the confirmation of performance and provision of the start signal for a next working step according to the prioritized sequence until all of the plurality of working steps of the prioritized sequence have been performed.

11. The method of claim 1, wherein at least one remote control unit of the plurality of remote control units is configured to control at least one of an imaging system, a robotic system, a member of medical personnel or a contrast agent injection system.

12. The method of claim 1, further comprising:
    providing an item of requirement information to a further, unassigned remote control unit, wherein the further, unassigned remote control unit is required in order to perform the prioritized sequence.

13. A coordination system for coordinating a plurality of remote control units on performance of a plurality of working steps, the coordination system comprising:
    at least one processor configured to cause the coordination system to
    receive a first provisional sequence of the plurality of working steps via an interface, the first provisional sequence including a sequence of the plurality of working steps, wherein at least one remote control unit of the plurality of remote control units, configured to perform the working step, is assigned to at least one working step of the plurality of working steps, aid, receive, via the interface, an item of information about a status of the assigned at least one remote control unit, prioritize the plurality of working steps at least based upon the first provisional sequence and the item of information, determine a prioritized sequence of the plurality of working steps based upon the prioritization, provide the prioritized sequence of the plurality of working steps via the interface, provide, via the interface, a start signal for the assigned at least one remote control unit, the start signal configured to initiate performance of the at least one working step by the assigned at least one remote control unit, receive, via the interface, a confirmation of performance for the initiated at least one working step, the confirmation of performance indicating that the initiated at least or working step is complete, and provide, via the interface, a lockout signal for at least one remote control unit of the plurality of remote control units that is not performing the initiated at least one working step until all of the plurality of working steps of the prioritized sequence have been performed.

14. A non-transitory computer program product storing a computer program loadable into a memory of a coordination system, the computer program including program parts for performing the method of claim 1 when the program parts are executed by at least one processor of the coordination system.

15. A non-transitory computer-readable storage medium storing program parts, readable and executable by at least one processor of a coordination system, for performing the method of claim 1 when the program parts are executed by the at least one processor.

16. The method of claim 2, the prioritizing includes taking account of dependencies between individual working steps of the plurality of working steps.

17. The method of claim 2, further comprising:
assigning a value characterizing significance to at least some of the plurality of working steps; and
assigning a high significance a safety-critical working step,
wherein the prioritizing includes taking account of the significance of the plurality of working steps.

18. The method of claim 2, further comprising:
receiving at least one second provisional sequence of the plurality of working steps,
wherein the at least one second provisional sequence includes an individualized sequence of a user of at least one remote control unit, and
wherein the prioritizing includes prioritizing the plurality of working steps based on the at least one second provisional sequence.

19. A computer-implemented method for coordinating a plurality of remote control units on performance of a plurality of working steps, the method comprising:

receiving a first provisional sequence of the plurality of working steps via an interface, the first provisional sequence including a sequence of the plurality of working steps, wherein at least one remote control unit of the plurality of remote control units, configured to perform the plurality of working steps, is assigned to at least one working step of the plurality of working steps;

receiving, via the interface, an item of information about a status of at least the assigned at least one remote control unit;

prioritizing, via a computing unit, the plurality of working steps at least based upon the first provisional sequence and the item of information;

determining, via the computing unit, a prioritized sequence of the plurality of working steps, via the interface;

providing an item of requirement information to a further, unassigned remote control unit, wherein the further, unassigned remote control unit is required in order to perform the prioritized sequence; and providing a start signal for the assigned at least one remote control unit, the start signal configured to initiate performance of the at least one working step by the assigned at least on remote control unit.

* * * * *